(12) United States Patent
Mullen

(10) Patent No.: US 6,346,297 B2
(45) Date of Patent: Feb. 12, 2002

(54) FRAGRANCE-CONTAINING PLASTIC COATING COMPOSITIONS FOR PAPER SUBSTRATES

(75) Inventor: Patricia A. Mullen, Babylon, NY (US)

(73) Assignee: Lenco Laboratories, LLC, Lindenhurst, NY (US)

( * ) Notice: Subject to any disclaimer, the term of this patent is extended or adjusted under 35 U.S.C. 154(b) by 0 days.

(21) Appl. No.: 09/896,972

(22) Filed: Jun. 29, 2001

Related U.S. Application Data

(62) Division of application No. 09/026,256, filed on Feb. 19, 1998, now Pat. No. 6,270,753.

(51) Int. Cl.⁷ .............................. B05D 3/00; B05D 3/02; A61L 9/00; A61K 9/00; A01N 25/00

(52) U.S. Cl. .................. 427/385.5; 424/76.1; 424/76.8; 424/400; 424/405; 424/484; 427/389.9; 427/393.1; 427/393.5; 427/412

(58) Field of Search .............................. 427/385.5, 389.9, 427/393.1, 393.5, 412; 424/76.1, 76.8, 400, 405, 484

(56) References Cited

U.S. PATENT DOCUMENTS

| 4,728,540 A | 3/1988 | Gasman |
| 5,087,664 A | 2/1992 | Sugino et al. |
| 5,227,406 A | 7/1993 | Beldock et al. |

OTHER PUBLICATIONS

Material Safety Data Sheet (MSDS)—NG0026 Therm–O–Line
Material Safety Data Sheet (MSDS)—NH–LB Low–Bleed

*Primary Examiner*—Shelly A. Dodson

(57) ABSTRACT

A fragrance-containing coating composition for paper substrates consists essentially of a polyvinyl chloride (PVC) plastisol and one or more fragrances, for example, an insect repellant. The PVC plastisol contains an adhesion promoter when the paper substrate is a calendered and/or coated paper substrate. The coating is fused at about 320° F. for 15–30 seconds. The coated paper is stored in barrier bags.

10 Claims, No Drawings

FRAGRANCE-CONTAINING PLASTIC COATING COMPOSITIONS FOR PAPER SUBSTRATES

RELATED APPLICATION

The present application is a divisional application of U.S. patent application Ser. No. 09/026,256, filed Feb. 19, 1998 now U.S. Pat. No. 6,270,753 and entitled FRAGRANCE-CONTAINING PLASTIC COATING COMPOSITIONS FOR PAPER SUBSTRATES.

BACKGROUND OF THE INVENTION

Paper has been used as a substrate for fragrances. Many examples of paper-based fresheners may be found on the market. However, the combination of fragrance(s), paper, and adhesives has not been feasible because fragrances are good solvents. When a fragrance is absorbed into the paper substrate, any adhesive bond with the paper substrate is destroyed. Either the adhesive is dissolved or it is softened to the point where the adhesion is lost.

Also, fragrance—impregnated paper exhibits problems of maintaining fragrance quality and controlled release. Therefore, there is a need for a fragrance-containing composition which can be coated on the surface of the paper to exhibit both controlled release of the fragrance and controlled absorption of the fragrance into the paper, and which will not penetrate to the back of the paper.

SUMMARY OF THE INVENTION

A fragrance-containing coating composition for paper substrates consists essentially of (a) a polyvinyl chloride plastisol and (b) one or more fragrances. The PVC plastisol is a dispersion which typically contains polymer and a plasticizer(s). The paper substrate can be a non-calendered, non-coated porous paper, a coated, non-calendered paper, or a calendered, optionally coated paper. When the paper is calendered and/or coated the polyvinyl chloride plastisol further contains an adhesion promoter.

The fragrance can be a fruit fragrance, a citrus fragrance, a floral fragrance, a woody fragrance, a leather fragrance, an oriental fragrance, a mint fragrance, and/or a food fragrance. A preferred fragrance is a mixture of insect repellents present in an amount sufficient to repel insects such as flies, mosquitos, and the like.

The coating composition may further consist essentially of a diluent as well as a component which has a synergistic effect when combined with the fragrance(s), e.g., dibutyl phthalate, a pigment, and/or a glitter.

The coating composition is applied at room temperature to at least one side of the paper substrate as a film. The coated paper substrate is rapidly heated at a temperature (e.g., 320° F.) and for a time (e.g., 15–20 seconds) sufficient to fuse the film to a clear coating and adhere it to the paper substrate without volatilizing the fragrance(s). The heated paper substrate is then cooled and stored until use in a barrier material such as polyethylene terephthate-coated polyethylene, or an aluminum-coated polyethylene. One side of the paper substrate may be coated with a pressure sensitive adhesive prior to coating when the preferred PVC plastisol is used.

The advantages of the above coating composition include good adhesion to the paper substrate, rapid drying under conditions which do not adversely affect the fragrance(s), clarity on drying which is important when graphics are present on the paper, and, compatibility with all paper grades. In addition, the plastisol has a low odor, has a low or no solvent content, is compatible with a wide range of fragrances, and will accept reasonably high levels of fragrance(s) and still retain the fragrance's notes.

This new plastic coating maintains fragrance quality, coating clarity, and paper adhesion and is useful for coating all grades of paper.

DESCRIPTION OF THE PREFERRED EMBODIMENTS

As used herein, the term "porous papers" refers to papers such as reply cards which are not calendered or coated.

As used herein, the term "papers with a vellum finish" refers to papers which are not calendered for smoothness. These papers have fibers protruding from the surface and are not coated.

As used herein, the term "coated paper substrates" refers to papers which are calendered for smoothness as well as papers which are calendered and clay-coated. Such papers may be matte finish, dull finish, regular finish, and cast-coated finish types. Papers with a matte finish are coated with an aqueous clay formulation consisting primarily of clay and optionally titanium dioxide. Papers with a dull finish are clay coated and calendered to provide a slight sheen on the surface. Papers with a regular finish have a heavy clay coating which is buffed and calendered for gloss. Papers with a cast-coated finish have the regular finish discussed above and are provided with additional calendering and/or coating to provide a mirror-like finish.

As used herein, the word "fragrance" refers to a mixture which provide a liquid with a pleasing odor. The fragrance may include two or more components and optionally a fixative or synergistic component which increases the fragrance's odor and permits the use of smaller amounts of the fragrance component(s).

As used herein the word "plastisol" refers to thermoplastics which require heat for fusion. Plastisols are dispersions which have a "milky" appearance. Prior to fusion, the plastisol film coated onto the substrate is "cloudy" or "milky". After fusion the plastisol film is completely clear. A "cloudy" or "milky" appearance indicates incomplete fusion.

Polyvinyl chloride (PVC) plastisols suitable for use herein contain polymers, plasticizers, and, when the paper is a smooth and/or coated, non-porous paper, an adhesion promoter or enhancer. The preferred polyvinyl chloride plastisol for smooth non-porous papers is a white or colored liquid which is available from Rutland Plastics Technologies, Inc. (Pineville, N.C.) under the trade name NG0026 Thermo-O-Line. It has a gel point of 165° F. and a flash point of >400° F. It should be stored at 65–97° F. to avoid "gelling". Pigment concentrates may be added to this plastisol in amounts of up to about 10–15% by weight if a tinted plastisol is desired.

Typically the coating thicknesses range from about 2–50 mils, preferably about 2–20 mils.

The maximum amount of fragrance which can be used is that amount which is soluble in the PVC plastisol and which does not destroy the film-forming properties. The minimum amount of fragrance is that amount which is required to provide a fragrance strong enough to last for the desired period of time. The amount of fragrance added to the PVC plastisol coating composition is 1.0 to about 20%, preferably about 6% to about 15%, most preferably about 13%, by weight, which amount will depend upon the particular fragrance(s) selected.

Fragrances in all odor categories are useful herein, for example, fruit fragrances such as strawberry, raspberry, peach, cherry, apple and pear; citrus fragrances such as orange, lemon, grapefruit, and lime; floral fragrances such as rose, hyacinth, lilac, lily-of-the-valley, calyx, osmanthus, orange blossom, apple blossom, rose, and freesia; woody fragrances such as cedarwood, sandalwood, oak, and pines; leather fragrances, i.e., dominant notes from the quinoline family; oriental fragrances such as musk, vanillin, laubdanum, and oak moss notes; aldehydic notes; mint fragrances such as spearmint and peppermint; and food fragrances such as vanilla, chocolate, chocolate mint, pizza, popcorn, barbecued meats (beef and chicken).

In many cases there is more than one way of achieving a particular fragrance type. A typical fragrance composition is composed of top-, middle-, and bottom-notes. The top-note (s) are the most volatile. The bottom-notes are the least volatile and are the residual on the surface which gives the fragrance a lasting quality. However, all of the notes contribute to the perception of the fragrance. For the type of use described herein, heat-stable fragrances are preferred.

A preferred fragrance area is insect repellant which have been formulated to contain a mixture of volatile natural and/or synthetic components which are referred to as fragrances because of their volatility and olfactory properties. As with the above fragrances, the repellant can be constructed of top-, middle-, and bottom-notes.

To be acceptable, the insect repellant must be long lasting and this quality is influenced by the PVC plastisol carrier. Preferably, the fragrance is formulated to contain more than one insect repellant. Insects which can be repelled include house flies, mosquitoes, yellow jackets, and ants.

Natural ingredients which act as insect repellants include salicylates, benzoates, lemon and orange oils, citronella oil, geraniol, terpineol, garlic oil, grapefruit oil, mints, southernwood, and tea tree oil.

The above insect repellents are used in amounts ranging from 0.3 to greater than 20% in a finished formula depending upon the repellency properties sought and the odor properties desired. For example, in the range of 0.3 to 1.0% one may use geraniol, lavender oil, camphor oil, and/or cinnamon oil; in the range of 1.0 to 10.0% one may use various acetates, citronella oil, lemon oil, orange oils, and terpineols; and in the range above 10% one may use lemon or orange oils and benzoates. Inert diluents such as glycols, alcohols, and/or phthalates, may be used for cost control.

Because the coating after fusion is glossy and transparent, it is particularly useful on printed paper substrates because the graphics can still be easily seen.

Preferably, a single coating having a thickness of about 2–50 mils., preferably about 2–20 mils., is applied at room temperature to one surface of the paper substrate. The thickness of the coating should not be thicker than that which can be fused during heating. If desired, more than one coating can be applied provided the coating is allowed to dry thoroughly between coatings. If desired, both sides of the paper substrate can be coated, in which case less fragrance will be needed to obtain the desired effect.

The coating is set by quickly heating the coated paper substrate. For example, the coated paper substrate is placed on a movable belt and quickly moved through a heating tunnel where the peak temperature is sufficient to fuse the film. Typically the peak temperature is about 320° F.; the exposure time to this temperature depends upon the thickness of the film. If the film is about 2 to about 4 mils in thickness, the fusion time will be about 15 seconds. The peak temperature and residence time in the tunnel should be sufficient to provide a clear, not "milky", coating.

After cooling the fused coated paper substrate can be cut into any desired shape. If desired, a tacky adhesive can be applied to the uncoated side of the paper substrate before or after the coating so that the coated product can be adhered to a person's clothing or other object. If not used immediately, the fragrance-coated substrate should be packaged so the fragrance does not prematurely evaporate from the coating. Evaporation is prevented by covering the coated paper substrate with a barrier material such as polyethylene terephthalate-coated polyethylene or aluminum-coated polyethylene, and the like.

EXAMPLE 1

This example describes the preparation of a fragrance which is a natural insect repellent and its inclusion in the polyvinyl chloride (PVC) plastisol which is sold under the trade name NG0026 Thermo-O-Line by Rutland Plastic Technologies.

The fragrance was obtained by mixing the following ingredients:

| Ingredient | Wt. % |
| --- | --- |
| Eucalyptus Oil | 0.3 |
| Cedarwood Oil | 0.7 |
| Citronella Oil | 10.0 |
| Pine Oil | 25.0 |
| Camphor Oil | 1.0 |
| Linalool | 1.0 |
| Linalyl Acetate | 1.0 |
| Lemon Oils | 10.0 |
| Phenylethyl Alcohol | 7.0 |
| Terpineol | 3.0 |
| Galbanum Oil | 1.0 |
| Benzyl Acetate | 15.0 |
| Turpentine | 2.0 |
| Patchouli | 5.0 |
| Benzyl Alcohol | 2.0 |
| Isoamyl Salicylate | 1.0 |
| Isopropyl Myristate | 2.0 |
| Isopropyl Palmitate | 4.0 |
| Dipropylene Glycol | 9.0 |
| | 100.0% |

A total of 10% (w/w) of the above fragrance was included in the PVC plastisol. One gallon was sufficient to coat 325 square feet of the paper.

The coating thickness was 4 mils. For testing 1 square inch portions of the paper were coated and the coating was fused at 320° F. for 15 seconds, cooled, and placed in a barrier bag. The coating parameters were chosen to provide a product life of 8 hours. The aroma was evaluated after storage in the barrier for 5 days. After storage in the barrier bags for 5 days, the coated paper samples were taken out and placed on a flat surface. The odor of the samples was evaluated over a period of 24 hours at which time the test was discontinued.

All of the papers listed below are calendered papers. Some are coated and some are embossed and uncoated. All are 65–80 lbs. stock.

The results are summarized below.

| Substrate | Organoleptic Evaluation |
| --- | --- |
| Textured Paper | |
| Ultrafelt Text (acid-, alum-, and rosin-free) | Good initial fragrance strength and good fragrance retention |
| Pageantry Cover Canvas (uncoated) | Good initial fragrance strength and good fragrance retention |
| Champion Cordwain Cover (uncoated) | Good initial fragrance strength and good fragrance retention |
| Champion Linen Cover | Good initial ,fragrance strength and good fragrance retention |
| Champion Felt Cover (alkaline sheets) | |
| Irish Linen Cover (acid-, alum-, and rosin-free) | Fragrance perceived was missing top notes initially and fragrance faded rapidly |
| George A. Whiting (acid-free, 100 % recycled) | Fragrance perceived was missing top notes initially and fragrance faded rapidly |
| Smooth Paper | |
| Augusta Bristol (0.007) | Good initial strength and good retention |
| Augusta Bristol (0.008) | Good initial strength and good retention |
| Augusta Bristol (0.009) | Good initial strength and good retention |
| Hammermill Cover Weyerhauser Husby Smooth Scott | Fragrance perceived was missing top notes initially and fragrance faded with time |
| Appleton Crystin Cover (coated paper) | Fragrance perceived was missing top notes initially and fragrance faded rapidly |
| Pageantry Cover Vellum (uncoated) | Fragrance perceived was missing top notes initially and fragrance faded rapidly |

EXAMPLE 2

The fragrance described in Example 1 is added at 10% (w/w) to an opaque, high viscosity, white polyvinyl chloride (PVC) plastisol which is sold under the trade name NH-LB LOW-BLEED by Rutland Plastic Technologies which has a gel point of 165° F. and a fusion temperature 320° F. The fragrance containing PVC plastisol is coated onto vellum, reply cards, or other uncalendered papers using an amount sufficient to provide a coating having a coating thickness of about 2–20 mils. The coating is fused at 320° F. for about 15 seconds, cooled, and stored in barrier bags.

Now that the preferred embodiments of the invention have been described in detail, various modifications and improvements thereon will become readily apparent to those skilled in the art. Accordingly, the spirit and scope of the present invention are to be limited only by the appended claims and not by the following specification.

What is claimed is:

1. A method of coating a paper substrate, which comprises the steps of:
    (a) applying at room temperature to at least one side of the paper substrate a film of a coating composition consisting essentially of (a) a polyvinyl chloride plastisol and (b) one or more fragrances;
    (b) rapidly heating the coated paper substrate at a temperature and for a time sufficient to fuse the film to a clear coating and adhere it to the paper substrate without volatilizing the fragrance(s); and
    (c) cooling the heated paper substrate; wherein the coating is applied in an amount sufficient to provide a continuous coating which will adhere to the paper and release the fragrance over time.

2. The method of claim 1, wherein the polyvinyl chloride is a dispersion containing polyvinyl chloride polymers, one or more plasticizers, and an adhesion promoter.

3. The method of claim 1, wherein the paper substrate is a porous paper substrate or a non-calendered paper.

4. The method of claim 1, wherein the paper substrate is a calendered and/or a coated paper substrate and wherein the coating further consists essentially of an adhesion promoter.

5. The method of claim 3, further comprising the step of packaging the coated paper substrate in a barrier material selected from the group consisting of polyethylene terephthate-coated polyethylene and an aluminum coated polyethylene.

6. The method of claim 1, further comprising the steps of coating the uncoated side of the paper substrates with a pressure sensitive adhesive.

7. The method of claim 1, wherein the heating is carried out at about 320° F. for a period of time sufficient to yield a clear coating.

8. A paper substrate coated with a fused polyvinyl chloride film containing an effective amount of one or more fragrances.

9. The paper substrate of claim 8, wherein the substrate which is coated is a non-calendered paper substrate and the fragrance is an insect repellent.

10. The paper substrate of claim 8, wherein the substrate which is coated is a calendered and/or coated paper substrate and the fragrance is an insect repellent.

* * * * *